United States Patent [19]
Kawata et al.

[11] Patent Number: 5,833,672
[45] Date of Patent: Nov. 10, 1998

[54] DOUBLE TUBE, BALLOON CATHETER PRODUCED BY USING DOUBLE TUBE, AND PROCESS FOR PRODUCING BALLOON CATHETER

[75] Inventors: Keiichi Kawata; Hidenobu Urata; Tetsuo Toyokawa; Kouichi Sakai; Masaru Uchiyama, all of Kanagawa, Japan

[73] Assignee: Nippon Zeon Co., Ltd., Tokyo, Japan

[21] Appl. No.: 849,316

[22] PCT Filed: Nov. 11, 1995

[86] PCT No.: PCT/JP95/02534

§ 371 Date: Jun. 10, 1997

§ 102(e) Date: Jun. 10, 1997

[87] PCT Pub. No.: WO96/18430

PCT Pub. Date: Jun. 20, 1996

[30] Foreign Application Priority Data

| Dec. 12, 1994 | [JP] | Japan | 6-332005 |
| Apr. 27, 1995 | [JP] | Japan | 7-127335 |
| Jul. 18, 1995 | [JP] | Japan | 7-203949 |

[51] Int. Cl.$^6$ ............................................. A61M 25/00
[52] U.S. Cl. ................................. 604/280; 604/96
[58] Field of Search ....................... 604/96, 264, 280, 604/282; 606/192, 194

[56] References Cited

U.S. PATENT DOCUMENTS

| 3,430,631 | 3/1969 | Abramsom | 604/282 |
| 4,909,787 | 3/1990 | Danforth | 604/95 |
| 5,085,649 | 2/1992 | Flynn | 604/282 |
| 5,100,379 | 3/1992 | Wendell | 604/51 |
| 5,195,962 | 3/1993 | Martin et al. | 604/43 |
| 5,222,949 | 6/1993 | Kaldany | 604/282 |
| 5,456,674 | 10/1995 | Bos et al. | 604/280 |
| 5,593,394 | 1/1997 | Kanesaka et al. | 604/282 |

FOREIGN PATENT DOCUMENTS

| 4-5966 | 1/1992 | Japan . |
| 4-224767 | 8/1992 | Japan . |
| 5-123403 | 5/1993 | Japan . |

*Primary Examiner*—Corrine M. McDermott
*Attorney, Agent, or Firm*—Armstrong, Westerman, Hattori, McLeland & Naughton

[57] ABSTRACT

A double tube from which a balloon catheter having a high rigidity and a low fluid resistance can be easily produced by means of an extruder or the like, an apparatus for producing the double tube, a balloon catheter produced by using the double tube, and a process for producing the balloon catheter are provided. The double tube comprises an outer tube having a lumen extending from the distal end to the proximal end, and an inner tube which is provided within the outer tube and has a lumen extending from the distal end to the proximal end, wherein a longitudinal member in the strip form is provided as a connecting member which continuously connects the inner surface of the outer tube to the outer surface of the inner tube in the axial direction. A balloon catheter can be easily produced by using this double tube. An apparatus for producing a double tube is also provided which comprises a first extruding means for extruding a resin for forming an outer tube portion, a second extruding means for extruding a resin for forming an inner tube portion, and a die for forming into tubes respectively from the resins extruded from the first extruding means and the second extruding means.

14 Claims, 16 Drawing Sheets

FIG. 3A    FIG. 3B    FIG. 3C
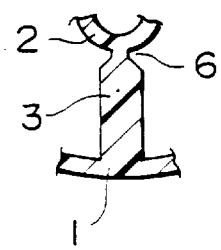 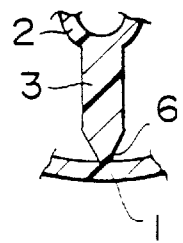 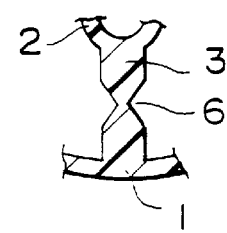
FIG. 3D    FIG. 3E    FIG. 3F
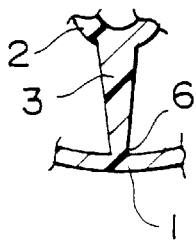 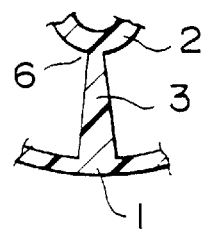 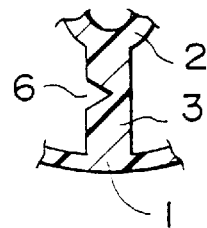

DOUBLE TUBE, BALLOON CATHETER PRODUCED BY USING DOUBLE TUBE, AND PROCESS FOR PRODUCING BALLOON CATHETER

FIELD OF ART

The present invention relates to a double tube, an apparatus for producing the double tube, a balloon catheter produced by using the double tube, and a process for producing the balloon catheter, and in more detail relates to a suitable double tube to easily produce a balloon catheter having a high rigidity, a suitable apparatus for producing the double tube, a balloon catheter produced by using the double tube, and a process for producing the balloon catheter.

BACKGROUND OF ART

An intra-aortic balloon pumping (what is called IABP) balloon catheter or a percutaneous transluminal coronary angioplasty (what is called PTCA) balloon catheter are comprised of a medical double tube having an outer tube and an inner tube which is provided within the outer tube. Also, in order to make it easy to insert the catheter into a body by saving the space to fold and accommodate a balloon film, the outer tube is comprised shorter than the inner tube at the distal end of the double tube. Further, the balloon film, which is fixed with the distal end of the outer tube and the distal end of the inner tube, is comprised to enable to be folded by wrapping around the inner tube.

In these medical double tubes for using the balloon catheter, the inner tube moves freely within a lumen of the outer tube, so is easily twisted, thereby making a high resistance of a fluid which flows in the lumen of the outer tube. Therefore, the response property of expanding and contracting movement of the balloon becomes lower. Also, in order to spread the area of cross section of the lumen, it is necessary to reduce the wall thickness of the tube, but in this case, the rigidity of the tube as a whole is reduced or easily kinked, thereby making such a problem as it becomes hard to insert into a vascular.

The inner tube of the balloon catheter is made to enable a guidewire to pass. The guidewire is passed through the narrow vascular cavity, the inner tube of a prior balloon catheter is passed through this guidewire, and thereby the balloon catheter is inserted into the vascular cavity. At that time, since the inner tube moves freely in the lumen of the outer tube, the guidewire becomes easily buckling or meandering, thereby making another problem that the resistance becomes higher when the guidewire is pushed into.

Further, the outer tube and the inner tube of the medical double tube used for the balloon catheter, being formed with a homogeneous material from the distal end to the proximal end, bends easily almost the same way in the range from the distal end to the proximal end. The inner tube of the balloon catheter is smaller than the outer tube in the outer diameter, so bends more easily than the outer tube. The distal end portion of the balloon catheter, which is held by only the inner tube extended from the distal end of the outer tube to the distal direction, is comprised more easier to bend in comparison with the proximal end held by the inner tube and the outer tube.

In this way, the inner tube extended from the distal end of the outer tube to the distal direction causes a kink easily around the distal end of the outer tube. Further, the distal end of the outer tube sometimes makes a trouble in respect of the insertion of the balloon catheter by colliding with the vascular cavity.

As a medical double tube, there are suggested such a balloon catheter that the outer diameter is smaller in the distal end portion than in the proximal end portion of the outer tube. There are also suggested such a balloon catheter obtained by forming the distal end portion by a soft material and the proximal end portion by a stiff material and tying both the ends up. In these balloon catheters, the insertion into the vascular cavity has been improved, the reinforcement, however, is not sufficient in the portion where the outer diameter is altered (the step portion) or the portion where the ends are tied up, so a kink is easily caused.

As a medical double tube, there are suggested such a medical double tube that a part of an outer surface of the inner tube is glued and affixed at a part of an inner surface of the outer tube. In this tube, the inner tube is no more twisted, so that the fluid resistance becomes lower. In this double tube, since the inner surface of the outer tube and the outer surface of the inner tube are glued, it is difficult to cut out the outer tube to be shorter so that only the inner tube should be extended to the distal end side. Therefore, the aforesaid medical double tube of a glued fixing type is produced by gluing the outer surface of the inner tube and the inner surface of the outer tube with an adhesive or the like.

A single tube or a multi-layer tube has been produced by an extruder or the like. The single tube is obtained by extruding a resin with a die having a circular hole. Also, the multi-layer tube is produced by using a die having a circular hole, extruding a resin for forming an inside layer side from the axial direction of the die, at the same time extruding a resin for forming a outside layer side from the direction out of a predetermined angle with respect to the axial direction of the die, forming a two-layer structure in the die, and extruding the resin remaining with the two-layer structure from the outlet of the die. The extrusion molding of the single tube or the two-layer tube, in order to save the domain of the lumen, has been keeping the lumen from collapsing and closing down by blowing a gas from the outlet of the die of the extruder. In the double tube, however, the lumen of the inner tube or the outer tube collapses and close down easily by the pressure fluctuation of the blowing gas. As a result, the medical double tube have not been enable to be mass-produced by the extrusion molding.

DISCLOSURE OF THE INVENTION

The present invention has as its object to provide a double tube from which a balloon catheter having a high rigidity and a low fluid resistance can be easily produced by means of an extruder or the like, an apparatus for producing the double tube, a balloon catheter produced by using the double tube, and a process for producing the balloon catheter.

Further, the present invention has as its object to provide a suitable medical double tube so as to produce a balloon catheter that makes it easy to transmit the maneuver force in the proximal end to the distal end and that makes it hard to kink and a balloon catheter produced by using the medical double tube, and besides provide a suitable medical double tube so as to produce a balloon catheter that makes it easy to insert the guide wire through the inner tube, and a balloon catheter produced by using the medical double tube.

The present inventors have been wholeheartedly engaged in studies in order to achieve these objects. Consequently they have discovered that the aforesaid objects can be achieved by using the double tube which is continuously provided between the inner surface of the outer tube and the outer surface of the inner tube with a connecting member in the strip form continued from the distal end to the proximal end. Thus the present invention has been perfected according to this knowledge.

Thus the double tube related to the present invention is characterized by comprising an outer tube having a lumen extending from the distal end to the proximal end, an inner tube which is provided within said outer tube and has a lumen extending from the distal end to the proximal end, and a connecting member continued from the distal end to the proximal end so that a part of said inner surface of the outer tube may be connected to a part of said outer surface of the inner tube, said connecting member being shaped to enable to separate the inner surface of the outer tube from the outer surface of the inner tube within the separable distance without damage.

Further, the double tube related to the different viewpoint of the present invention is characterized that the flexural rigidity of the outer tube or the inner tube is larger in the proximal end side than in the distal end side.

The apparatus for producing the double tube related to the present invention is characterized by comprising a first extruding means for extruding a resin for forming an outer tube portion of the double tube, a second extruding means for extruding a resin for forming an inner tube portion of the double tube, and a die for forming tubes respectively out of the resins extruded from said first extruding means and said second extruding means.

In the aforesaid die, there are formed a first circular hole where the resin extruded from the first extruding means passes from the backward to the forward of the die, and a second circular hole where the resin extruded from the second extruding means passes from the backward to the forward of the die.

The second circular hole is provided inside said first circular hole.

From the forward outlet to the backward of either of said first circular hole and said second circular hole, there are formed a slit in an inside hole wall of the first circular hole or in an outside hole wall of the second circular hole so that said slit forms a connecting member which continuously connects the resin for forming the inner tube portion to the resin for forming the outer tube portion.

The first extruding means is connected to the die so that the resin extruded from the first extruding means can pass from the backward to the forward through the first circular hole and the second extruding means is connected to the die so that the resin extruded from the second extruding means can pass from the backward to the forward of the second circular hole.

The balloon catheter related to the present invention is characterized by comprising the double tube and the balloon;

said double tube comprising an outer tube having a lumen extending from the distal end to the proximal end, an inner tube which is provided within said outer tube and has the lumen extending from the distal end to the proximal end, and a connecting member which continuously extends from the distal end to the proximal end so that a part of inner surface of said outer tube can connect to a part of the outer surface of said inner tube;

said connecting member being shaped to enable to separate the inner surface of the outer tube from the outer surface of the inner tube within the separable distance without damage;

said outer tube being shorter than the inner tube in length and the distal end of the inner tube is extended in the distal direction from the distal end of the outer tube;

said balloon being formed with a cylindrical film; and the one end of the film being affixed to the distal end of inner tube and the other end to the distal end of the outer tube.

Further, the process for producing the balloon catheter related to the present invention comprises the steps of cutting an outer tube of a double tube into a circular sliced portion at just the preferable distance from the distal end of the outer tube, the double tube being comprised of the outer tube having a lumen extending from the distal end to the proximal end, an inner tube which is provided within said outer tube and has a lumen extending from the distal end to the proximal end, and a connecting member continued from the distal end to the proximal end so that a part of an inner surface of said outer tube is connected to a part of the outer surface of said inner tube, separating a part of said outer tube from a part of said connecting member in a region from the distal end of the outer tube to said circular sliced portion, removing the part of said outer tube in the region from the distal end of said outer tube to said circular sliced portion, and affixing the one end of a cylindrical film as a balloon at said circular sliced portion of said outer tube and the other end of the film at the distal end of said inner tube.

In the double tube according to this invention, the outer tube and the inner tube are provided and the inner surface of the outer tube and the outer surface of the inner tube are continuously connected by the connecting member continued from the distal end to the proximal end.

The connecting member is one shaped to enable to hold the inner surface of the outer tube and the outer surface of the inner tube with the preferable distance. The connecting member is generally a longitudinal member continued from the distal end to the proximal end. The shape of cross section of the connecting member comprised of the longitudinal member is not particularly limited, but there are given polygon such as a rectangle, a square, a rhombus, a trapezium, a triangle, and a pentagon; circle such as a perfect round and an ellipse; and so on. The connecting member comprised of the longitudinal member is one shaped for extending in the longitudinal direction of the tube, for example in the stick or strip form.

The connecting member comprised of the longitudinal member is generally made of the same material as the outer tube or the inner tube, however, so as to make it easy to separate the outer tube from the inner tube, preferably the different material from that for forming the outer tube or the inner tube.

The connecting member has the height that is generally 0.05~3 mm, preferably 0.1~2 mm in the distance between the outer surface of the inner tube and the inner surface of the outer tube.

The connecting member is, in order to make it easy to separate the outer tube from the inner tube, preferably made as small as possible in thickness, generally 0.03~0.82 mm, preferably 0.05~0.6 mm.

As the connecting member, in order to make an easy separation of the outer tube or the inner tube, preferably use is made of the longitudinal member having a notch portion 6 continued along the direction of a longitudinal axis. The size of the notch portion is not particularly limited. The notch portion is provided between the outer surface of the inner tube and the inner surface of the outer tube. In order to make it easy to separate the outer tube, preferably this notch portion is provided to lie adjacent to the outer surface of the inner tube or the inner surface of the outer tube (Referring to FIG. 3A, 3B, 3D, or 3E).

The outer tube and the inner tube are tubes having a lumen communicated from the distal end to the proximal end of the same. The inner tube is arranged within the outer tube.

The Young rate of the material for forming the outer tube has been smaller in the distal end portion than in the proximal end portion. The Young rate in this case is obtained in accordance with the flexural experimental method of a hard plastic with the Japanese Industrial Standards (JIS) K7203. The Young rate in the distal end portion of the outer tube is generally 1000~20000 kgf/cm$^2$, preferably 2000~10000 kgf/cm$^2$. The Young rate in the proximal end portion of the outer tube is generally 2000~30000 kgf/cm$^2$, preferably 3000~18000 kgf/cm$^2$. The difference of the Young rate between the distal end portion and the proximal end portion of the outer tube is generally 1000~16000 kgf/cm$^2$.

Further, the flexural rigidity in the outer tube is smaller in the distal end portion than in the proximal end portion. The rate of the flexural rigidity in this case is obtained in accordance with the flexural experimental method of a hard plastic with the Japanese Industrial Standards K7203. The flexural rigidity in the distal end portion of the outer tube is generally 30~200 kgf·cm$^2$, preferably 40~150 kgf·cm$^2$. The flexural rigidity in the proximal end of the outer tube is generally 60~1000 kgf·cm$^2$, preferably 80~800 kgf·cm$^2$. The difference of the flexural rigidity between the distal end portion and the proximal end portion of the outer tube is generally 30~800 kgf·cm$^2$, preferably 40~760 kgf·cm$^2$.

The Young rate of the material for forming the outer tube or the flexural rigidity of the outer tube may be formed to become smaller by steps from the proximal end portion to the distal end portion, but preferably is formed to become smaller continuously from the proximal end portion to the distal end portion in order to prevent a kink.

The Young rate of the material for forming the inner tube or the flexural rigidity of the inner tube may be about the same from the distal end to the proximal end, considering the insertability into the vascular cavity, preferably is formed smaller in the distal end portion than in the proximal end portion the same as the outer tube. The Young rate in the distal end portion of the inner tube is generally 1000~20000 kgf/cm$^2$, preferably 2000~80000 kgf/cm$^2$. The Young rate in the proximal end portion of the inner tube is generally 2000~30000 kgf/cm$^2$, preferably 3000~18000 kgf/cm$^2$. The difference of the Young rate between the distal end portion and the proximal end portion of the inner tube is generally 1000~16000 kgf/cm$^2$.

Further, the flexural rigidity in the distal end portion of the inner tube is generally 10~100 kgf·cm$^2$, preferably 20~80 kgf·cm$^2$. The flexural rigidity in the proximal end portion of the inner tube is generally 30~300 kgf·cm$^2$, preferably 40~150 kgf~cm$^2$. The difference of the flexural rigidity between the distal end portion and the proximal end portion of the inner tube is generally 20~200 kgf/cm$^2$, preferably 20~130 kgf/cm$^2$.

The Young rate of the material for forming the inner tube or the flexural rigidity of the inner tube may be formed to become smaller by steps from the proximal end portion to the distal end portion, but preferably is formed to become smaller continuously from the proximal end portion to the distal end portion in order to prevent a kink.

The inner tube and the outer tube where the Young rate or the flexural rigidity is formed to become smaller from the proximal portion to the distal end portion, may be comprised of a two-layer tube where the outside layer of the tube is formed with the resin of a lower hardness and the inside layer of the tube with the resin of a higher hardness. In this case, the thickness of the outside layer may be formed thick in the distal end portion and thin in the proximal end portion, while the thickness of the inside layer may be formed thin in the distal end portion and thick in the proximal end portion. To the contrary, the inner tube or the outer tube may be comprised of a two-layer tube where the inside layer of the tube is formed with the resin of a lower hardness and the outside layer of the tube with the resin of a higher hardness. In this case, the thickness of the inside layer is formed thick in the distal end portion and thin in the proximal end portion, while the thickness of the outside layer is formed thin in the distal end portion and thick in the proximal end portion.

The inner tube or the outer tube may be comprised of a wire-braided tube, where the line density of the braided wire is rough in the distal end portion and dense in the proximal end portion. Moreover, the inner tube or the outer tube may be comprised of a tube which is constructed by alternately disposing a soft material strip portion and a stiff material strip portion extending in the strip form in the axial direction. The number of the soft material strip portions may be made a lot in the distal end portion and a few in the proximal end portion. Moreover, the width of the circumferential direction of this soft material strip portion may be formed long in the distal end portion and short in the proximal end portion.

In the inner tube or the outer tube, according to the present invention, by making the Young rate or the flexural rigidity smaller in the distal end portion than in the proximal end portion, the following effect is obtained. That is, when the balloon catheter using the double tube is inserted into the vascular cavity from the distal end portion of the same, the damage against the vascular wall is decreased by the distal end of the balloon catheter, and the multiplier effect with the connecting member makes a kink hard to occur. Further, the Young rate is high in the proximal end side, so the maneuver force in the proximal end portion is easy enough to transit to the distal end side.

Accordingly, the insertion of the balloon catheter using the double tube into the vascular cavity is easier.

In the double tube according to the present invention, a space surrounded with the outer tube and the inner tube is used in order that a liquid or a gas for expansion of the balloon of the balloon catheter may pass through it. In the double tube of the present invention, the outer tube and the inner tube are continuously connected by the connecting member. Even if being twisted or rolled, the inner tube is not snaked within the outer tube. Therefore, the passing resistance of a liquid or a gas for expansion of the balloon becomes lower. As a result, when the balloon of the balloon catheter is expanded and contracted repeatedly, the response thereof especially improves.

Further, in the double tube of the present invention, the outer tube and the inner tube are continuously connected by the connecting member, which functions as a frame connecting member, thereby increasing the rigidity of the tube as a whole.

As the balloon catheter, generally, the double tube in which the inner tube is longer than the outer tube and is extended from the distal end to the distal direction of the outer tube is used.

In the double tube of the present invention, the continuous connection between the outer tube and the inner tube can be easily canceled by cutting off the connecting member. Therefore, the method of the present invention comprises the steps of cutting the outer tube into a circular sliced portion, separating the outer tube from the connecting member in a region from the distal end to the circular sliced portion, separating the connecting member from the inner tube in a region from the distal end to the circular sliced portion of the outer tube, and removing the outer tube, and thereby the double tube where the inner tube is longer than the outer tube and extended in the distal direction from the distal end (the circular sliced portion) can be easily obtained without any damages to the inner tube.

Moreover, in the double tube of the present invention where the connecting member has the notch portion continued along the direction of its longitudinal axis, the separation can be easily made in this notch portion, which enables to make the outer tube more easily cut off.

In the apparatus for producing the double tube of the present invention, the resin extruded from the first extruding means forms the outer tube portion through the first circular hole and the resin extruded from the second extruding means forms the inner tube portion through the second circular hole. This enables to effectively keep the lumen of the inner tube or the outer tube from collapsing or transforming by the pressure fluctuation of a blowing gas. Since there are also formed a slit from the forward outlet of the first circular hole or the second circular hole to the backward, at the forward outlet of the first circular hole and the second circular hole, the resins having passed through them connects with each other, which enables to mass-produce the double tube continuously provided with the connecting member between a part of the outer surface of the inner tube and a part of the inner surface of the outer tube.

BRIEF DESCRIPTION OF THE DRAWINGS

In the drawings,

FIG. 3A is a view showing one mode example in a sectional shape of the connection of the double tube of the present invention;

FIG. 3B is a view showing another mode example in a sectional shape of the connection of the double tube of the present invention;

FIG. 3C is a view showing another mode example in a sectional shape of the connection of the double tube of the present invention;

FIG. 3D is a view showing another mode example in a sectional shape of the connection of the double tube of the present invention;

FIG. 3E is a view showing another mode example in a sectional shape of the connection of the double tube of the present invention;

FIG. 3F is a view showing another mode example in a sectional shape of the connection of the double tube of the present invention;

DESCRIPTION OF THE PREFERRED EMBODIMENTS

Figure 1:
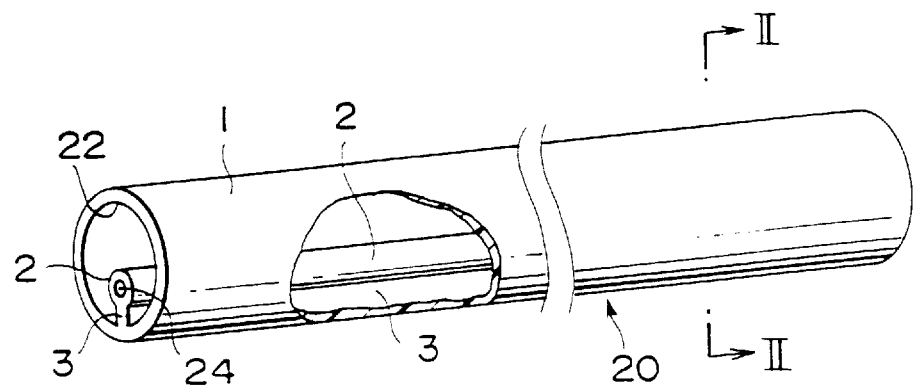
FIG. 1 is a part of a breaking view of a double tube according to a first embodiment of the present invention.

Below, double tubes according to preferred embodiments of the present invention will be explained in more detail referring to the drawings.

Figure 2:
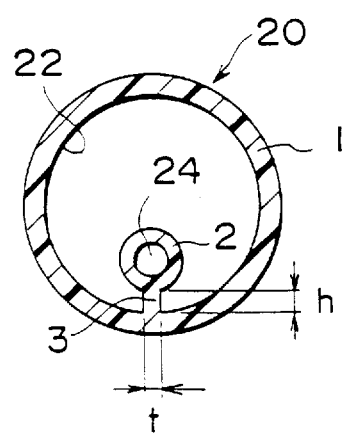
FIG. 2 is a cross-sectional view taken along the line II—II shown in FIG. 1.

As shown in FIGS. 1 and 2, the double tube 20 according to the first embodiment of the present invention is comprised of an outer tube 1 having a lumen 22 extending from the distal end to the proximal end and an inner tube 2 which is arranged within the lumen 22 of the outer tube 1 and has a lumen 24 extending from the distal end to the proximal end.

The inner diameter of the outer tube 1 is generally 0.4~6 mm, preferably 0.5~4 mm, and the thickness is generally 0.3~0.8 mm, preferably 0.05~0.6 mm.

Since the outer tube 1 is the portion contacted with a biological tissue by inserting into the vascular cavity, generally the material used for the outer tube 1 is a biocompatibility material.

As the biocompatibility material, there are given polyamide resin, polyimide resin, fluorine resin, polyvinyl chloride resin, polypropylene resin, polyethylene resin, polyurethane resin, or the like. Note that, contrast media, antibacterial agent, or the like may be compounded with the biocompatibility material.

The inner diameter of the inner tube 2 is generally 0.2~3 mm, preferably 0.3~2 mm, and the thickness is generally 0.3~0.8 mm, preferably 0.05~0.6 mm.

The inner tube does not contact directly with the biological tissue but gets the invasion of a biofluid into the lumen in it, so is formed by the biocompatibility material the same as the outer tube.

A connecting member 3 for continuously connecting the inner surface of the outer tube 1 and the outer surface of the inner tube 2 is the longitudinal member.

A transverse cross-section of the connecting member 3 comprised of the longitudinal member is not particularly limited, but use may be made of polygon such as a rectangle, a square, a rhombus, a trapezium, a triangle, and a pentagon; circle such as a perfect round and a ellipse; and so on (Referring to FIGS. 3A~3F.). When the double tube is processed into the balloon catheter, in order to make it easy to separate the inner tube 2 from the outer tube 1, the transverse cross-section of the connecting member 3 is preferably a triangle, a pentagon, a rhombus, or the like.

Generally the connecting member 3 comprised of the longitudinal member is made of the same material for forming the outer tube 1 or the inner tube 2. In order to make an easy separation of the outer tube 1 and the inner tube 2, preferably use is made of the different material from the one for forming the outer tube 1 or the inner tube 2.

At least any one of the inner tube 2 and the outer tube 1 is preferably comprised of a tube, where soft material strip portions and stiff material strip portions, extending in a strip form in an axial direction, are alternately disposed in a circumferential direction, and a number of the soft material strip portions are made large in the distal end of any one of the inner tube 2 and the outer tube 1, respectively, and small in the proximal end of any one of the inner tube 2 and the outer tube 1, respectively.

The connecting member 3 has the height "h" so that the distance between the outer surface of the inner tube 2 and the inner surface of the outer tube 1 is generally 0.05~3 mm, preferably 0.1~2 mm.

The thickness "t" of the connecting member 3 is preferably made as small as possible so as to make it easy to separate the outer tube 1 from the inner tube 2, generally 0.03~0.8 mm, preferably 0.05~0.6 mm.

For an easy separation of the outer tube 1 and the inner tube 2, as the connecting member 3, as shown in FIGS. 3A~3F, the longitudinal member having a notch portion 6 continued along the direction of a longitudinal axis is preferably used.

The size of the notch portion 6 is not particularly limited. Generally the notch portion 6 is provided between the outer surface of the inner tube 2 and the inner surface of the outer tube 1, however, for an easy separation of the outer tube 1, is preferably provided to lie adjacent to the outer surface of the inner tube 2 or the inner surface of the outer tube 1.

The double tube 20 in this embodiment is generally produced by an extruding method. Specifically, the material is supplied to one extruder, by which the material is extruded from a nozzle. As another method, the material for the outer tube is supplied to one extruder and the material for the inner tube is supplied to another extruder. By using these two extruders, each material is extruded from the nozzle at the same time or something like that, and thereby the double tube 20 is formed. If the latter method with two extruders is used, both materials for the outer tube and the inner tube are pushed into the portion of the connecting member 3, at which an interface is formed, thereby making an easy separation of the outer tube 1 in a connecting portion.

Note that, the shape of the nozzle may be one that the inner tube 2, the outer tube 1, and the connecting member 3 are extruded at the same time. At the nozzle, so as to save the lumens of the inner tube 2 and the outer tube 1, a gas blow opening may be provided.

Figure 4:
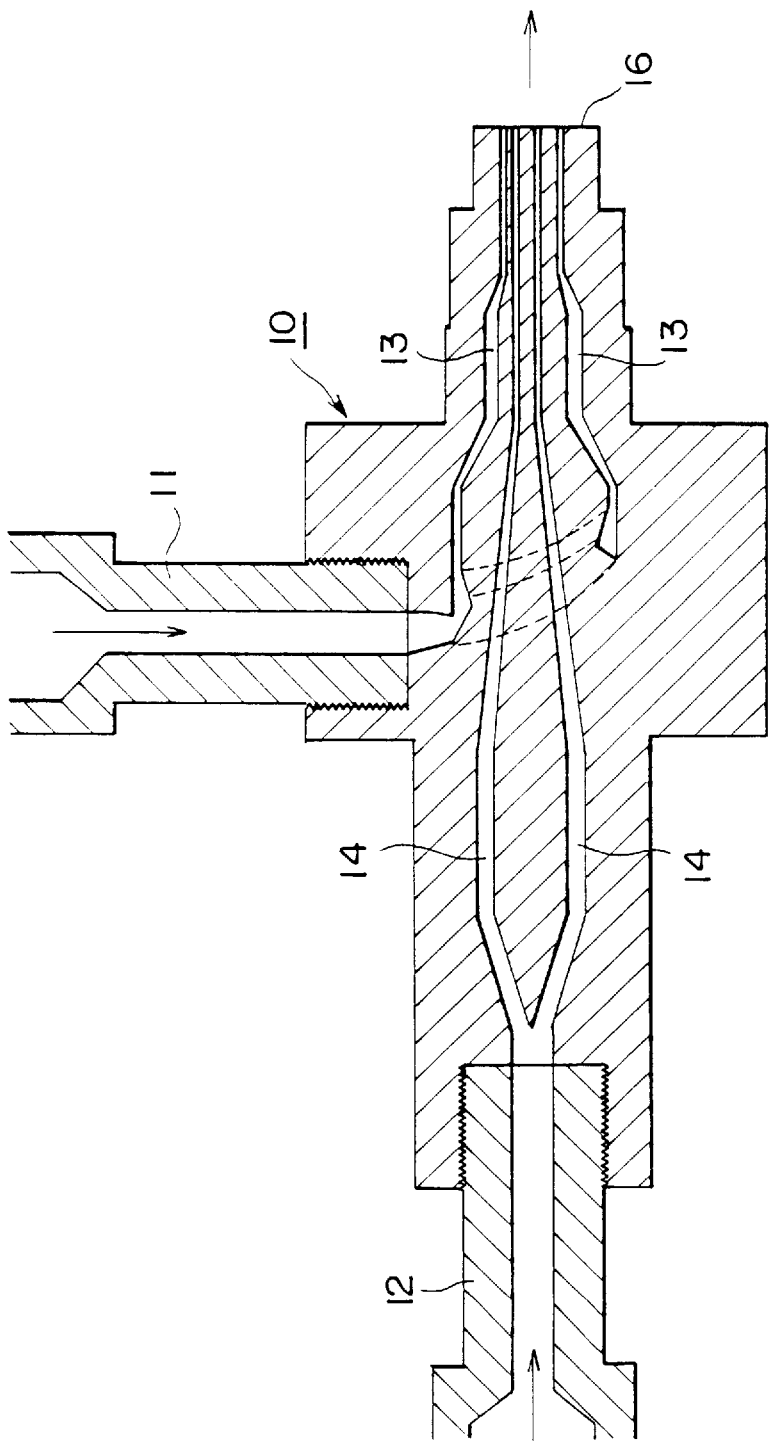
FIG. 4 is a view showing a section of one mode of an apparatus for producing a double tube of the present invention.

As shown in FIG. 4, a preferable apparatus for producing to industrially mass-product the double tube of the present invention comprises a first extruding means 11 for extruding the resin for forming the outer tube portion of the double tube, a second extruding means 12 for extruding the resin for forming the inner tube portion of the double tube, and a die 10 for forming into tubes respectively out of the resins extruding from the first extruding means and the second extruding means.

The first extruding means 11 and the second extruding means 12 are used for pressing into the resin from the backward of the die and extruding the resin from the forward outlet of the die. The first extruding means 11 and the second extruding means 12 are able to be connected to the die so that the resin extruded from each of them can respectively pass through the circular hole disposed in the die.

As the first extruding means 11 and the second extruding means 12, generally, are given the extruders having the extruding mechanism such as a screw, a gear, a planetary screw, and a rotary disc. For a specific example of the extruders are given such as a single-axis extruder, a two-axis extruder, a vent type extruder, a kneading extruder, a double extruder, a multiaxes extruder, an oblique multiaxes extruder, a planetary screw extruder, a gear type extruder, a ram style extruder, a rotary disc extruder, etc.

The die 10 is a mold for shaping the resins extruded from said first extruding means 11 and the second extruding means 12 into the desired form.

As shown in FIGS. 4 and 5, according to the apparatus for producing of the present invention, the die 10 comprises a first circular hole 13 for passing the resin extruded from the first extruding means 11 and a second circular hole 14 for passing the resin extruded from the second extruding means 12. The second circular hole 14 is arranged inside the first circular hole 13 (inside of the ring). Generally, the first circular hole 13 and the second circular hole 14 are not substantially communicated with each other. Since the first circular hole 13 and the second circular hole 14 are not substantially communicated with each other, when the resin is extruded from the first extruding means 11, the one is delivered through the first circular hole 13 and thereby the outer tube 1 portion can be formed, while when the resin is extruded from the second circular hole 12, the one is delivered through the second circular hole 14 and thereby the inner tube 2 portion can be formed. Here, substantially not being communicated means that just a little portion provided with the slit mentioned later can be communicated.

In the die 10 according to the apparatus for producing of the present invention, as shown in FIGS. 5A–5D, FIGS. 6A–6D, and FIGS. 7A and 7B, at the first circular hole 13 or the second circular hole 14, there are formed slit 15a–15e for forming the connecting member 3 which continuously connects a part of the inner surface of the outer tube 1 and a part of the inner surface of the inner tube 2 from the forward outlet of the die 10 to the backward. The length of the slit 15a–15e is generally in the range less than about 10 mm, preferably in the range less than 5 mm from the forward outlet 16 to the backward of the die 10, in order to keep the lumen of the inner tube 2 or the outer tube 1 from collapsing or closing. The slit 15a–15e are in general communicated with the first circular hole 13 or the second circular hole 14.

As shown in FIGS. 5C, 5D, 6A, and 6B, if the slit 15b or 15c is provided in either of the first circular hole 13 or the second circular hole 14, the bottom of the slit 15 is preferably remained so that the bottom may be just adjacent to the second circular hole 14 or the first circular hole 13. The adjacent distance thereof may be generally in the range less than 1 mm, preferably in the range less than 0.5 mm.

Figure 5A:
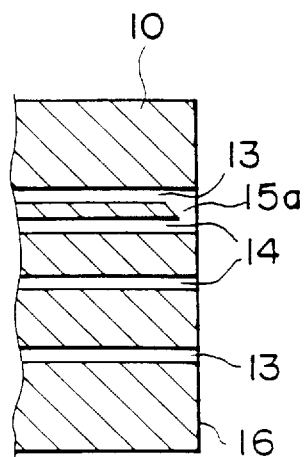
FIG. 5A is a vertical cross-sectional view showing one mode of a die used in the apparatus for producing a double tube of the present invention.
Figure 5B:
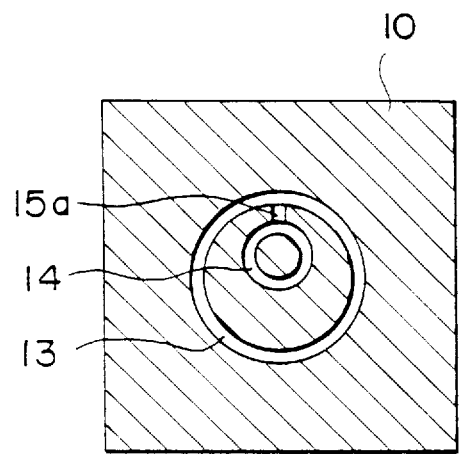
FIG. 5B is a transverse cross-sectional view of the die shown in FIG. 5A.
Figure 5C:
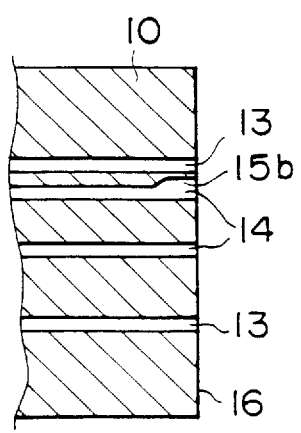
FIG. 5C is a vertical cross-sectional view showing another mode of the die used in the apparatus for producing the double tube of the present invention.
Figure 6A:
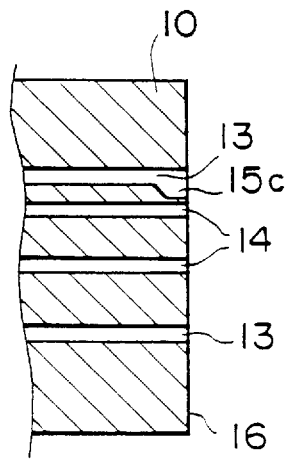
FIG. 6A is a vertical cross-sectional view showing another mode of the die used in the apparatus for producing the double tube of the present invention.
Figure 6B:
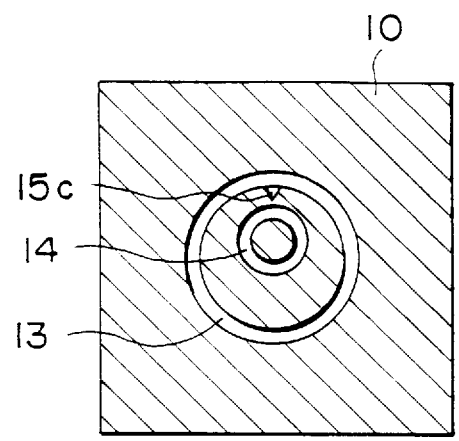
FIG. 6B is a transverse cross-sectional view of the die shown in FIG. 6A.
Figure 6C:
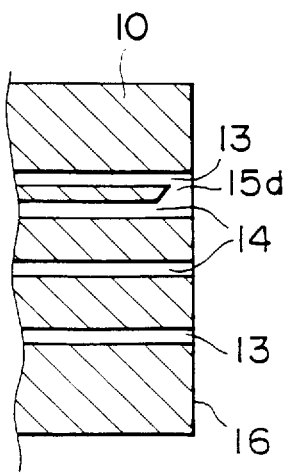
FIG. 6C is a vertical cross-sectional view showing another mode of the die used in the apparatus for producing the double tube of the present invention.
Figure 6D:
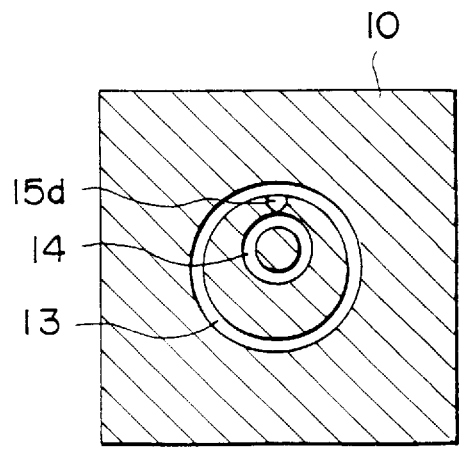
FIG. 6D is a transverse cross-sectional view of the die shown in FIG. 6C.
Figure 7A:
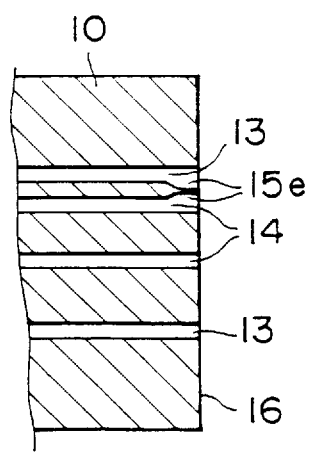
FIG. 7A is a vertical cross-sectional view showing another mode of the die used in the apparatus for producing the double tube of the present invention.
Figure 7B:
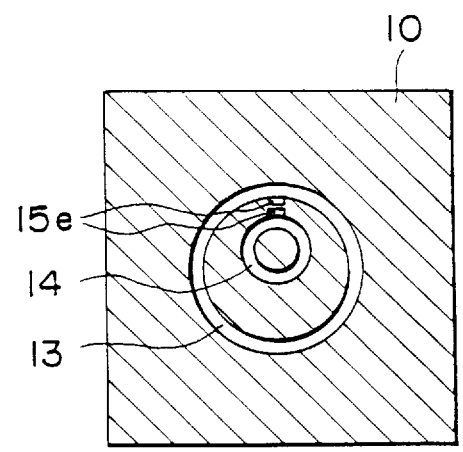
FIG. 7B is a transverse cross-sectional view of the die shown in FIG. 7A.

Further, as shown in FIGS. 7A and 7B, if the slits 15e are provided in both of the first circular hole 13 and the second circular hole 14, the bottoms of the slits 15e are preferably remained so that both the bottoms approach to each other. The distance thereof may be generally in the range less than 1 mm, preferably in the range less than 0.5 mm. Preferably the slit is formed so as to remain the bottom in such a thin range so that a part of the inner surface of the outer tube 1 can be connected with a part of the outer surface of the inner tube 2 at the connecting portion. Note that, as shown in FIGS. 5A, 5B, 6C, and 6D, it is more preferable that the slits 15a and 15d are provided so as to communicate with both the first circular hole 13 and the second circular hole 14 from a point of view that the inner tube and the outer tube are certainly connected with each other by the connecting member.

The size of the first circular hole 13 or the second circular hole 14 can be suitably chosen in conformity with the outer diameter and the inner diameter of the outer tube 1 and the inner tube 2 of the double tube.

Figure 5D:
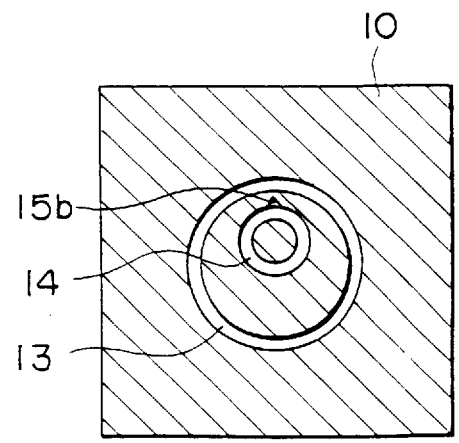
FIG. 5D is a transverse cross-sectional view of the die shown in FIG. 5C.

The shape of the slits 15a–15e is not particularly limited, but may be the one which enables to communicate with the first circular hole 13 or the second circular hole 14 and which connects continuously a part of the inner surface of the outer tube 1 to a part of the outer surface of the inner tube 2 in the axial direction. Observing the die from the front in the axial direction, for example, the shape of slit may be a square as shown in FIG. 5B, a triangle as shown in FIG. 5D or FIG. 6B, or a pentagon or a rhombus as shown in FIG. 6D.

At the time of processing the double tube into the balloon catheter, in order to make an easy separation between the inner tube 2 and the outer tube 1, preferably the slit is shaped in a triangle, a pentagon, or a rhombus so that the double tube in a section shown in FIGS. 3A–3F can be obtained.

The width and depth of the slits 15a to 15f may be designed in accordance with the size of the connecting member 3 which continuously connects the outer tube 1 to the inner tube 2 in the axial direction.

Note that, in the die 10 shown in FIG. 4, the gas blow openings (not shown) may be provided inside the second circular hole 14 (inside of the ring), and provided outside the second circular hole 14 (outside of the ring) and inside the first circular hole 13 (inside of the ring).

According to the apparatus for producing in this embodiment, generally, the first circular hole 13 and the second circular hole 14 of the die 10 are, to be approximately horizontal, attached at each of the first extruding means 11 and the second extruding means 12. Note that, according to the apparatus for producing of the present embodiment, in order to make the dimensional stability of each lumen of the inner tube 2 and the outer tube 1 of the double tube higher, preferably the die 10 is attached at the first extruding means 11 and the second extruding means 12 so that the slits 15a to 15e may be vertical in the upper direction against the second circular hole 14.

Figure 8A:
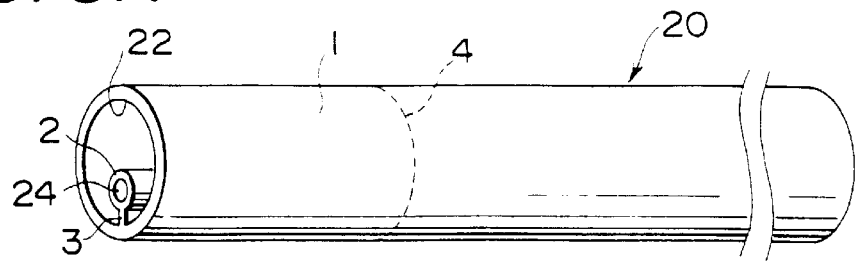
FIGS. 8A to 8D are schematic views showing the process for producing the balloon catheter using the double tube shown in FIG. 1.

The process for producing the balloon catheter using the double tube 20 in this embodiment is shown in FIGS. 8A to 8D. First, as shown in FIG. 8A, the outer tube 1 is cut into a circular sliced portion at the position 4 of the desired distance from the distal end of the outer tube 1 of the double tube 20. At that time, the inner tube 2 should not be cut at the same time.

Figure 8B:
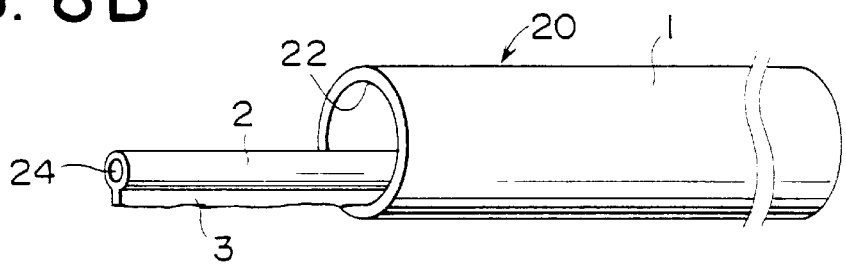
Figure 8C:
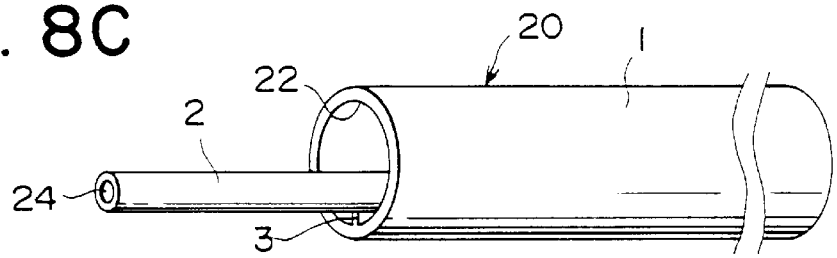
Figure 8D:
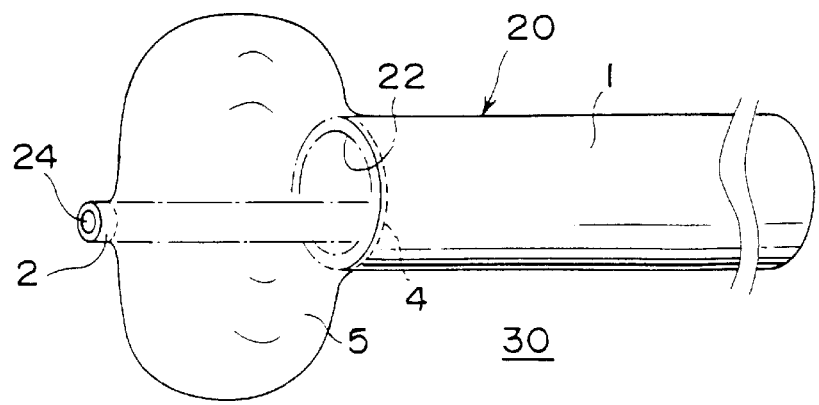

Next, as shown in FIG. 8B, the portion from the distal end of the outer tube 1 to said circular sliced portion 4 and the one from the distal end of the connecting member 3 to said circular sliced portion 4 are separated, and the former portion is removed. Next, as shown in FIG. 8C, the connecting member 3 remained around the inner tube 2 which is projected from the distal end is completely removed. Next, as shown in FIG. 8D, the portion from said circular sliced portion 4 to the distal end portion of the inner tube 2 is covered with a cylindrical film 5 to connect and fix the one end of this film to the circular sliced portion 4 of the outer tube 1 and the other end of the same to the distal end of the inner tube 2.

In the step of cutting the outer tube 1 into the circular sliced portion, each of the position 4 to be circular sliced is different depending on the balloon catheter, but is generally a distance of 10~500 mm and preferably a distance of 50~40 mm from the distal end.

The means for cutting into the circular sliced portion is not particularly limited, but for example, a pipecutter, a knife, or the like can be adopted as the means for cutting the wall of the outer tube 1.

In the step of separating each portion, the one portion from the distal end of the connecting member 3 to said circular sliced portion 4 and the other portion from the distal end of the outer tube 1 to said the circular sliced portion, the means for separating is not particularly limited, but for example, there are means for tearing and separating, means for cutting and separating by a knife or the like, and so on.

By processing through these steps, the portion of the outer tube 1 from the distal end of the outer tube 1 to said circular sliced portion can be removed.

Note that, in the step shown in FIG. 8C, in order to smooth the outer surface of the inner tube 2 which is projected extending in the distal direction from the distal end of the outer tube 1, the connecting member 3 remained in the outer surface of the inner tube 2 has removed as well, however, according to the present invention, may be remained in this portion.

After removing the outer tube 1 which is from the distal end of the same to said circular sliced portion 4, the portion from the circular sliced portion 4 of the outer tube 1 (hereinafter, also referred to as the distal end 4 of the outer tube 1) to the distal end portion of the inner tube 2 is covered with the cylindrical film. The one end of this film 5 is connected and fixed to the distal end of the outer tube 1 and the other end to the distal end of the inner tube 2, and thereby the balloon catheter 30 is produced.

The cylindrical film 5 is for forming the balloon. The thickness of the film 4 is generally 5~150 μm. The area of the film is determined so that, in a state where this film is expanded after forming the balloon, its volume generally becomes 0.1~80 cm$^3$ and the balloon generally becomes 1~30 mm in outer diameter and 10~500 mm in length in the longitudinal direction.

As the film 5, use is made of the material superior in resistance to flexural fatigue and antithrormbusibility. For example, polyurethane, natural rubber, or the like is given.

The film 5 is affixed to the distal end of the outer tube 1 and to the distal end of the inner tube 2 by heat bonding or adhesion.

In the double tube of this embodiment, since the outer tube and the inner tube are continuously connected by the connecting member, even though being twisted or rolled, the inner tube is not snaked within the outer tube. Therefore, becomes lower the passing resistance of a liquid or a gas in the lumen 22 for expansion of the balloon comprised of the film 5. The outer tube 1 and the inner tube 2 are continuously connected by the connecting member 3, which functions as a frame member, thereby making the rigidity of the double tube 20 as a whole higher.

In the double tube 20 of this embodiment, the continuous connection between the outer tube 1 and the inner tube 2 can be easily canceled by cutting off the connecting member 3. Accordingly, by doing in arbitrary order a step of cutting the outer tube into a circular sliced portion; a step of separating the outer tube which is from the distal end to the circular sliced portion from the connecting member; and a step of separating the connecting member which is from the distal end to the circular sliced portion of the outer tube from the inner tube and removing only the outer tube not for damaging the inner tube, and thereby the inner tube which is longer than the outer tube and exposed from the distal end of the outer tube can be easily obtained.

Moreover, according to the double tube of this embodiment, as shown in FIGS. 3A to 3F, where the connecting member 3 has the notch portion 6 continued along the direction of its longitudinal axis, the separation can be easily made in this notch portion 6, so the outer tube can be more easily cut off.

Figure 9:
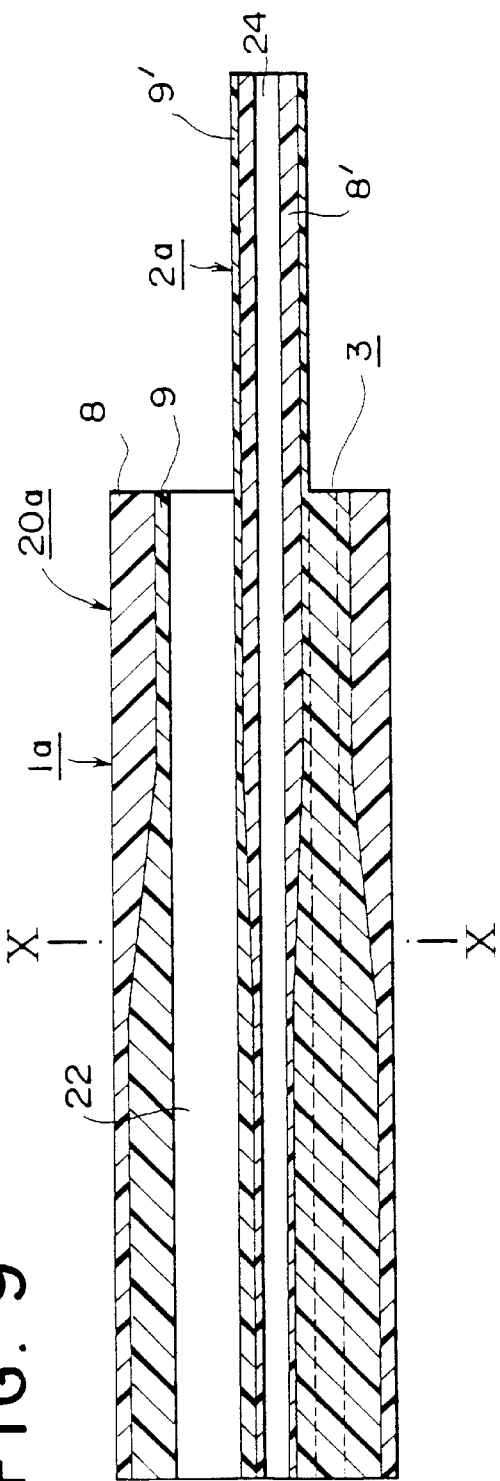
FIG. 9 is an axial sectional view of the double tube related to another embodiment of the present invention.
Figure 10:
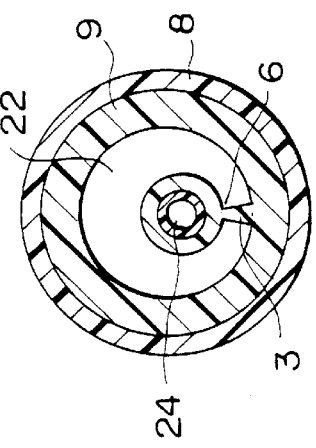
FIG. 10 is a cross-sectional view taken along the line X—X of the double tube shown in FIG. 9.

In the double tube 20a shown in FIGS. 9 and 10 shows another embodiment of the present invention. The outer tube 1a of the double tube 20a is a laminated tube of a two-layer tube where an inside layer 9 of the tube is comprised by a stiff material and an outside layer 8 of the tube by a soft material. In the distal end thereof, the thickness of the inside layer 9 is smaller than that of the outside layer 8, and in the proximal end thereof, the thickness of the inside layer 9 is larger than that of the outside layer 8. The Young rate in the distal end of the outer tube 1a according to this embodiment is about 4500 kgf/cm$^2$ and that in the proximal end is about 11000 kgf/cm$^2$. Also, the flexural rigidity in the distal end of the outer tube 1a according to this embodiment is about 80 kgf·cm$^2$ and that in the proximal end is about 500 kgf·cm$^2$.

The inner diameter of the inner tube 2a is generally 0.2~3 mm, preferably 0.3~2 mm and the thickness is generally 0.03~0.8 mm, preferably 0.05~0.6 mm.

The inner tube 2a does not contact directly with the biological tissue but gets the invasion of a biofluid into the lumen in it, so is formed by the biocompatibility material the same as the outer tube 1a.

In the inner tube 2a according to this embodiment, the Young rate or the flexural rigidity in the distal end portion is lower than that in the proximal end portion. The inner tube 2a shown in FIG. 9 is a laminated tube of a two-layer where an outside layer 9' of the tube is comprised by a stiff material and an inside layer 8' of the tube by a soft material. In the distal end, the thickness of the outside layer 9' is smaller than that of the inner tube 8', and in the proximal end, the thickness of the outside layer 9' is larger than that of the inside layer 8'.

The Young rate in the distal end of the inner tube 2a according to this embodiment shown in FIG. 9 is about 4000 kgf/cm$^2$ and that of the proximal end is about 9000 kgf/cm$^2$. Also, the flexural rigidity of the distal end of the inner tube 2 is about 40 kgf·cm$^2$ and that of the proximal end is about 100 kgf·cm$^2$.

In the double tube shown in FIG. 9, the inner surface of the outer tube 1a and the outer surface of the inner tube 2a are continuously connected through the connecting member 3 (Referring to FIG. 10). As shown in FIG. 10, in this connecting member 3, there have been also formed the same notch portion 6 as the aforesaid embodiment.

According to this embodiment, in order to make the Young rate or the flexural rigidity of the outer tube 1a (or the inner tube 2a) comprised by the laminated tube to be larger from the distal end to the proximal end, the outside layer 8 (or the inside layer 8') of the tube is comprised of the resin with a lower hardness and the inside layer 9 (or the outside layer 9') of the tube is comprised of the resin with a higher hardness. Further, the thickness of the outside layer 8 (or the inside layer 8') is made thick in the distal end portion and thin in the proximal end portion and that of the inside layer 9 (or the outside layer 9') is made thin in the distal end portion and thick in the proximal end portion. According to the present invention, however, in order to make the Young rate or the flexural rigidity of the outer tube 1a or the inner tube 2a to be larger from the distal end to the proximal end, these tubes may be comprised of a wire-braided tube, where the line density of the braided wire is rough in the distal end portion and dense in the proximal end portion.

In the laminated tube of a two-layer where the outside layer 8 of the tube is comprised of the resin with a lower hardness and the inside layer 9 of the tube is comprised of the resin with a higher hardness, the laminated tube is comprised so that the thickness of the outside layer 8 may be thick in the distal end portion and thin in the proximal end portion and the thickness of the inside layer 9 may be thin in the distal end portion and thick in the proximal end portion. Such a laminated tube, for example, can be produced as follows. The material of the outside layer for the outer tube or the inner tube is supplied into one extruder and the material of the inside layer for the outer tube or the inner tube is supplied into another extruder. By using these two extruders, each of the materials is extruded from the same nozzle at the same time. At that time, the extruding velocities of both the extruders are changed each other, so as to adjust the thickness between the inside layer and the outside layer and form a single tube to be an outer tube or an inner tube. After that, a double tube is obtained by connecting the outer tube and the inner tube with an adhesive or the like. The double tube used in the embodiment shown in FIG. 1 was produced by using this method.

Further, by using the plural extruders, the material of the outside layer for the outer tube, the material of the inside layer for the outer tube, the material of the outside layer for the inner tube, and the material of the inside layer for the inner tube are respectively supplied into each of them. Each of the materials is, at the same time, extruded from the same nozzle. By changing the extruding velocity of each extruder so as to adjust the thickness between the inside layer and the outside layer, the double tube is formed and obtained. In the embodiment shown in FIG. 9, this method was used.

Figure 11:
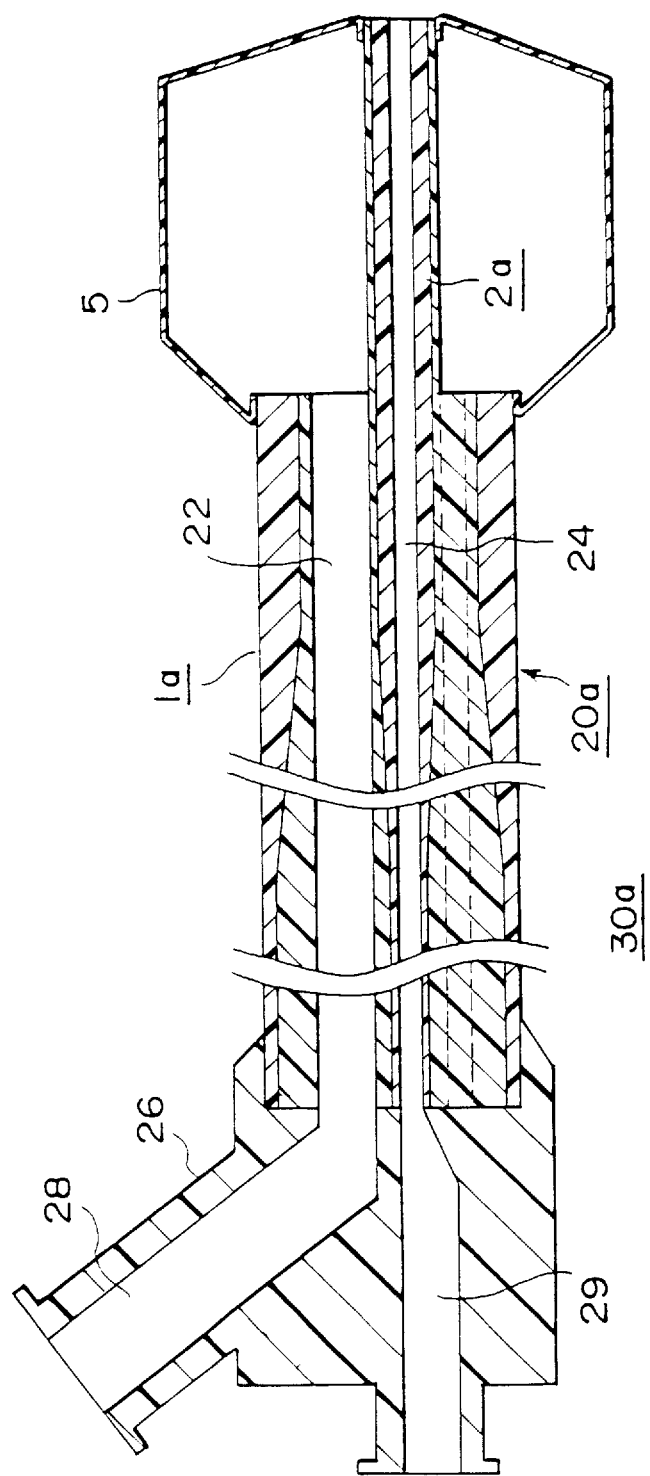
FIG. 11 is a cross-sectional view taken along the axial direction of the balloon catheter obtained by using the double tube shown in FIG. 9.

A balloon catheter 30a of the present invention shown in FIG. 11 has the double tube 20a where the distal end of the inner tube 2a is more extended in the distal direction than the distal end of the outer tube 1a as shown in FIG. 9 and has a balloon 5. The balloon 5 is formed by the cylindrical film, where the one end is affixed at the distal end of the inner tube 2a and the other end at the distal end of the outer tube 1a. The distal end of the inner tube 2a is generally extended 10~500 mm, preferably 50~400 mm form the distal end of the outer tube 1a in the direction of the distal end.

The cylindrical film for forming the balloon 5 covers from the distal end of the outer tube to the distal end of the inner tube. The one end of the film is affixed at the distal end of the outer tube and the other end at the distal end of the inner tube. The fixing method is not particularly limited, but for example, welding, adhesion, or the like can be used. As a result, the inside of the balloon 5 becomes an enclosed space for communicating with the lumen 22, where a fluid from a fluid port 28 of the bifurcated tube connector 26 which is connected with the proximal end of the double tube 20a is introduced or released, thereby making it possible to expand or contract the balloon. Note that, a blood communicating port 29 of the connector 26 is communicated with the lumen 24 of the inner tube 2a, which makes the fluctuation in the blood pressure or the like of a blood measurable from the distal end of the inner tube 2a. Further, through this port 29, the guidewire is inserted.

Figure 12:
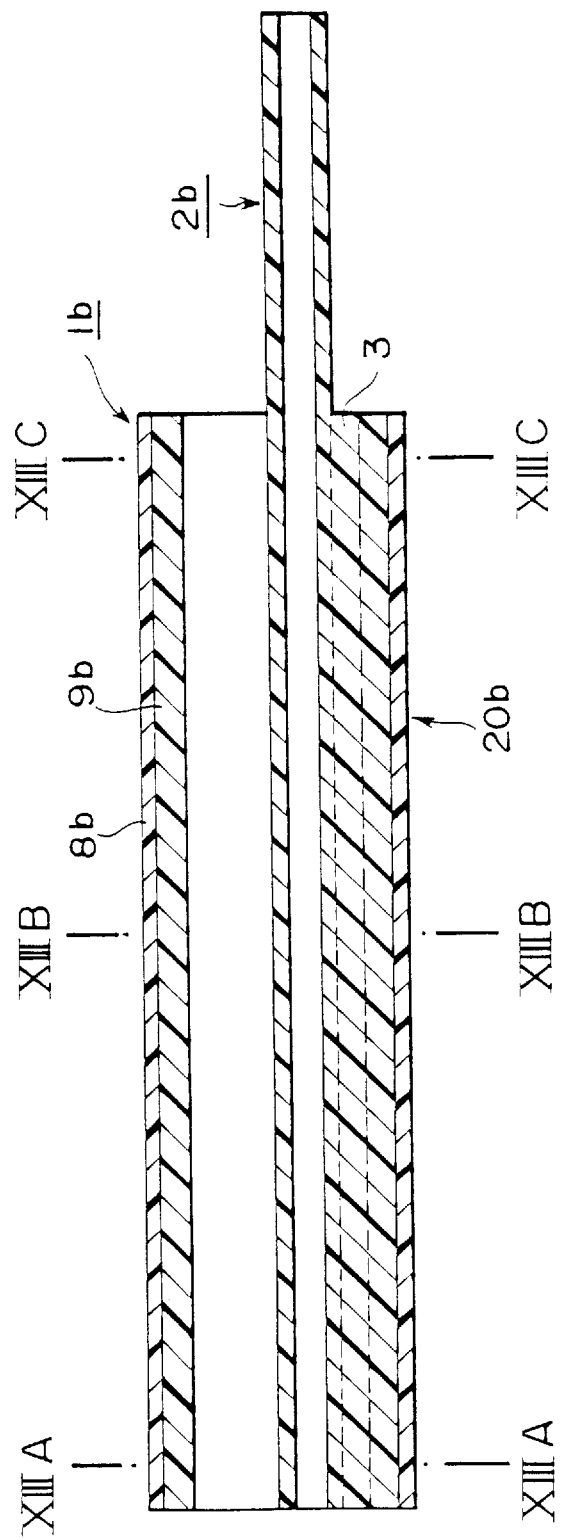
FIG. 12 is an axial sectional view of the double tube related to another embodiment of the present invention.
Figure 13A:
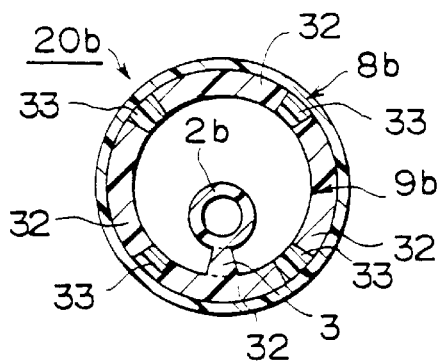
FIGS. 13A to 13C are cross-sectional views taken along the lines XVIIIA—XVIIIA, XIIIB—XIIIB, and XIIIC—XIIIC of the double tube shown in FIG. 12.
Figure 13B:
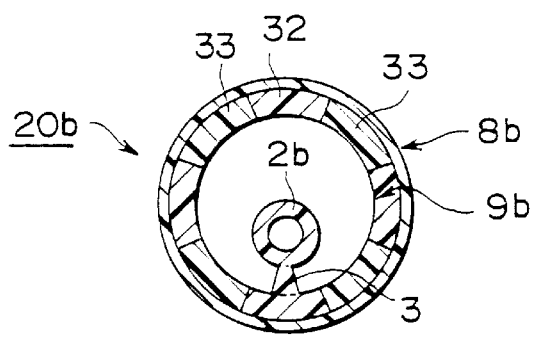
Figure 13C:
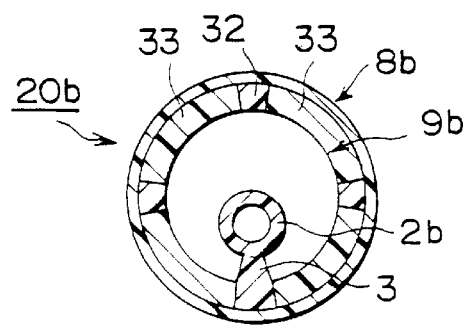

In a double tube 20b shown in FIG. 12, the outer tube 1b is comprised of the soft material and the stiff material. An outside layer 8b of the tube is comprised of the soft material and an inside layer 9b of the tube is comprised so that a soft material 33 and a stiff material 32 may be alternately layered in the circumferential direction (Referring to FIGS. 13A to 13C). In the way of laminating the inside layer 9b of the tube, as shown in FIG. 13C, the layer of the soft material 33 is made quantitatively more than that of the stiff material 32 in the distal end portion (the length in the circumferential direction is long). As shown in FIGS. 13A and 13B, the layer of the soft material 33 is made quantitatively less than that of the stiff material 32 in the proximal end portion (the length in the circumferential direction is short). Accordingly, the Young rate or the flexural rigidity of the double tube 20b in this embodiment becomes larger in the proximal end portion than in the distal end portion.

As shown in FIGS. 12, 13A to 13C, the inner tube 2b is connected with the inner surface of the outer tube 1b through a connecting portion 3 and is comprised of the stiff material 32 in the embodiment shown in FIG. 12. The inner tube 2b, however, may be comprised of the soft material 33 in order to make the flexibility of the inner tube 2b higher.

Figure 14:
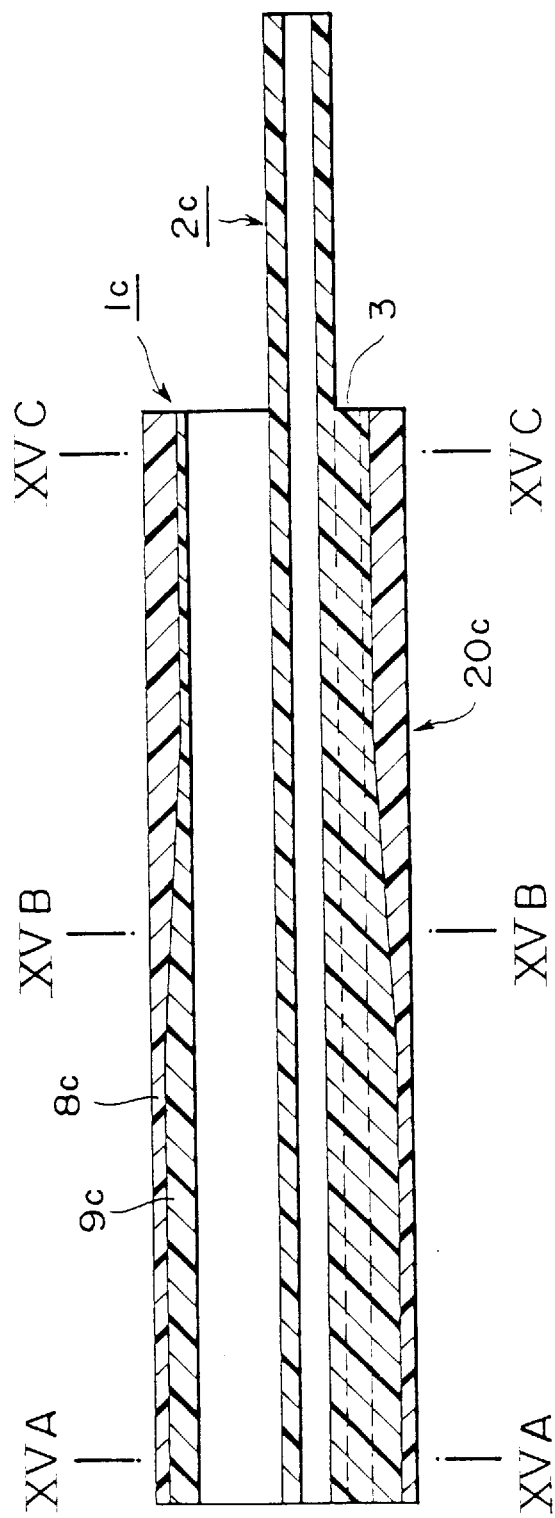
FIG. 14 is an axial sectional view of the double tube related to another embodiment of the present invention.
Figure 15A:
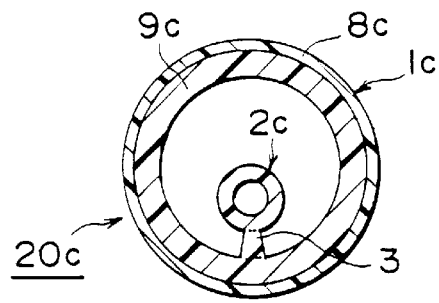
FIGS. 15A to 15C are cross-sectional views taken along the lines XVA—XVA, XVB—XVB, and XVC—XVC of the double tube shown in FIG. 14.
Figure 15B:
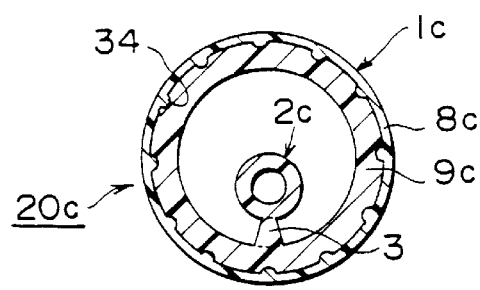
Figure 15C:
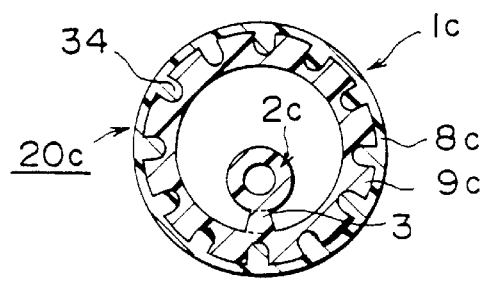

In a double tube 20c shown in FIG. 14, the outer tube 1c is comprised of a soft material and a stiff material. An outside layer 8c of the tube is comprised of the soft material and an inside layer 9c of the tube is comprised of the stiff material. In the proximal end portion of the outer tube 1c, as shown in FIG. 15A, the outside layer 8c is thin in compared with the inside layer 9c in thickness. As shown in FIGS. 15B and 15C, in the distal end portion of the outer tube 8c, a rib structure 34 is formed. The structure 34 is designed so that the soft material for forming the outside layer 8c may project into a clearance of the stiff material for forming the inside layer 9c. The height for the soft material projecting into the stiff material is made higher toward the distal end portion. As a result, the Young rate or the flexural rigidity of the double tube 20c of this embodiment becomes larger in the proximal end portion than in the distal end portion.

The inner tube 2c is connected with the inner surface of the outer tube 1c through the connecting portion 3 and is comprised of the same stiff material as the inside layer 9c in the embodiment shown in FIG. 14. In order to make the flexibility of the inner tube 2c higher, the inner tube 2c may be comprised of the soft material or may be provided with the rib structure 34 of the soft material and the stiff material in the same way as the outer tube 1c.

Figure 16:
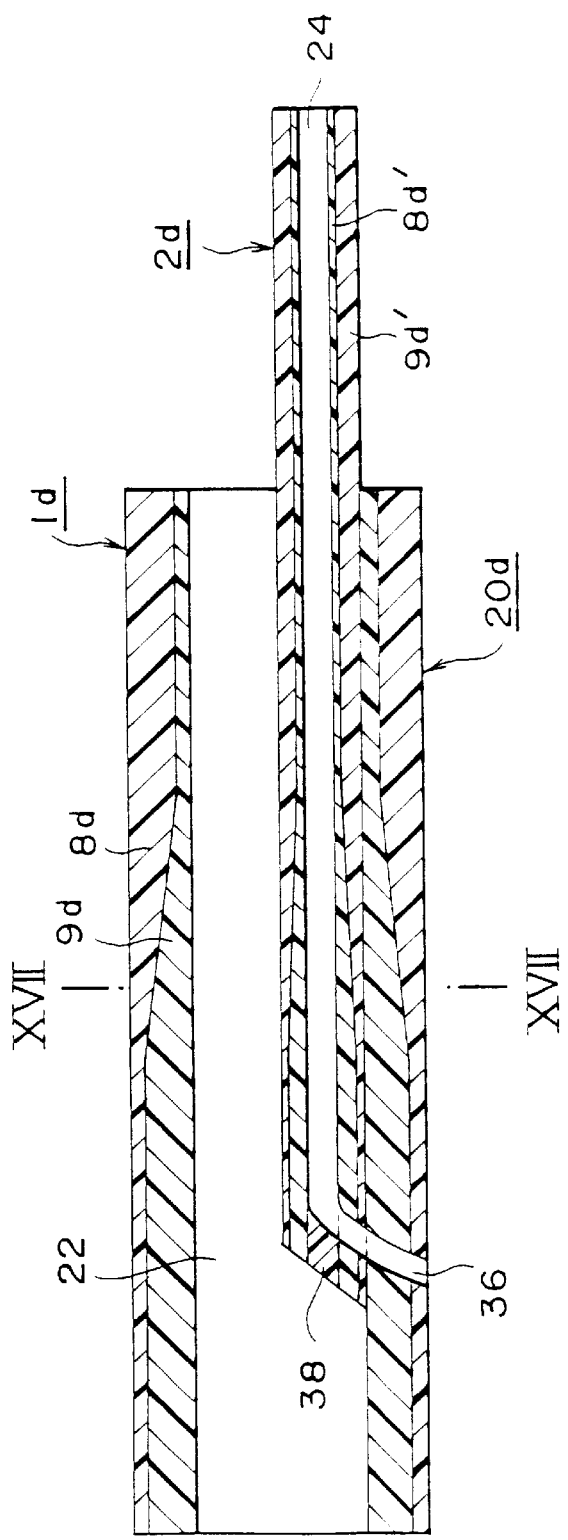
FIG. 16 is an axial sectional view of the double tube related to another embodiment of the present invention.
Figure 17:
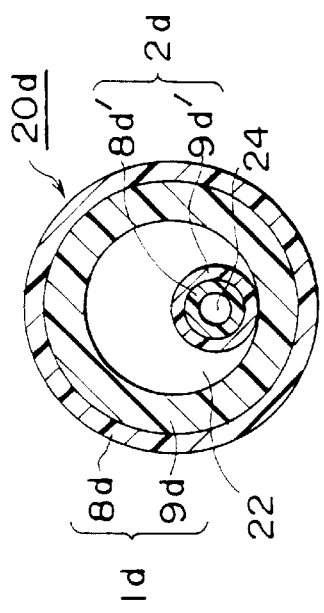
FIG. 17 is a cross-sectional view taken along the line XVII—XVII of the double tube shown in FIG. 16.
Figure 18:
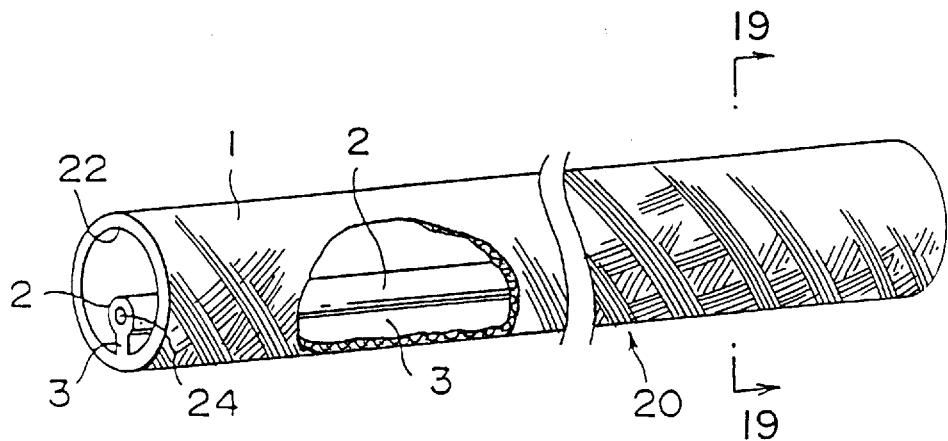
FIG. 18 is a part of a breaking view of the double tube according to the first embodiment of the present invention, wherein the outer tube 1 is shown as being made of a braided wire material.
Figure 19:
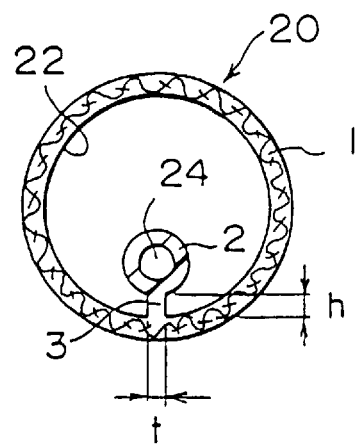
FIG. 19 is a cross-sectional view taken along line 19—19 of FIG. 18.
Figure 20:
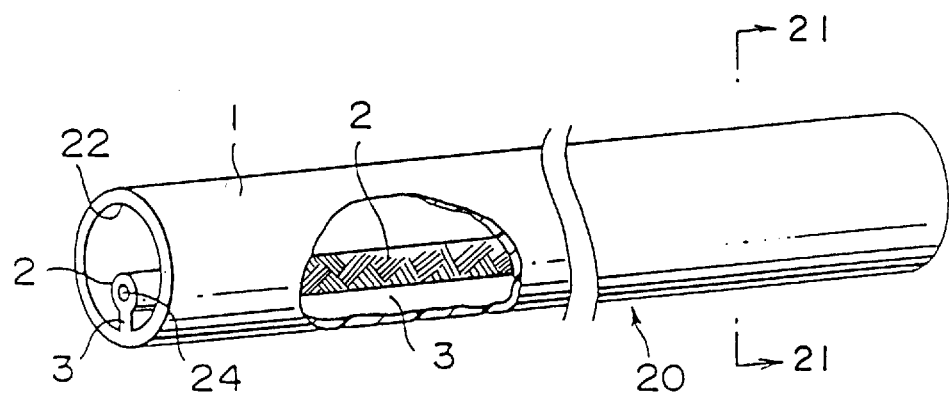
FIG. 20 is a part of a breaking view of the double tube according to the first embodiment of the present invention, wherein the inner tube 2 is shown as being made of a braided wire material.
Figure 21:
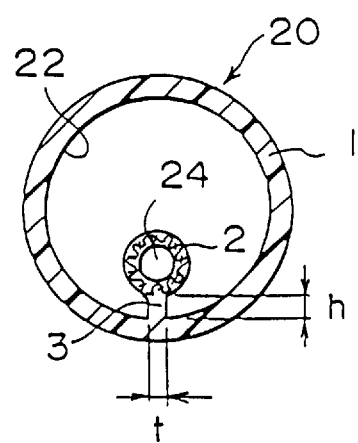
FIG. 21 is a cross-sectional view taken along line 21—21 of FIG. 20.

A double tube 20d according to the embodiment shown in FIGS. 16 and 17 is a modification of the double tube 20a shown in FIGS. 9 and 10, where the connecting portion 3 shown in FIGS. 9 and 10 is eliminated and the outer circumference of an tube 2d is bonded or adhered onto the inner circumference of an outer tube 1d. Further, the proximal end of the lumen 24 of the inner tube 2d is blocked by a plug 38, and is communicated with a guidewire taking-out port formed in the distal end side of the outer tube 1d.

In the embodiment shown in FIGS. 16 and 17, the method which makes the flexural rigidity or the Young rate in the distal end side of the outer tube 1d and the inner tube 2d smaller in comparison with the proximal end side is the same method as the embodiment shown in FIGS. 9 and 10. Namely, the outside layer 8d, the inside layer 9d, the outside layer 9d', and the inside layer 8d, shown in FIGS. 16 and 17 are respectively comprised of the same material and sectional shape along the axial direction as the outside layer 8, the inside layer 9, the outside layer 9', and the inside layer 8' shown in FIGS. 9 and 10.

According to the double tube 20d of the embodiment shown in FIGS. 16 and 17, there have been formed the guidewire taking-out port 36 on the way of the double tube 20d. The guidewire is taken out from it. Along the guidewire, the balloon catheter having the double tube 20d can be inserted inside of the vascular cavity. As a result, in comparison with the balloon catheter using the double tube 20a of the embodiment shown in FIG. 9, the balloon catheter using the double tube 20d of this embodiment can be maneuvered by using comparatively a short guidewire. A short guidewire is superior in maneuverability at the treatment.

In the double tube of the embodiment shown in FIGS. 9 to 17, since the Young rate in the distal end portion of the inner tube and the outer tube is made smaller than in the proximal end portion, when the balloon catheter using the medical double tube is inserted into the vascular cavity from its distal end portion, the damage against the vascular cavity decreases by the distal end of the balloon catheter. Further, in the embodiment shown in FIGS. 9 to 15, the multiplier effect with the connecting member 3 makes a kink hard to occur. Further, in the double tube of embodiment shown in FIGS. 9 to 17, the maneuver force in the proximal end portion is easy enough to transit to the distal end side because of a high Young rate in the proximal end side, and thereby the double tube is superior in maneuverability. Therefore, the balloon catheter using the medical double tube is easily inserted into the vascular cavity. Further, the double tube of the embodiment shown in FIGS. 1 to 15 has the connecting member 3, so the double tube having the inner tube where the distal end side is projected can be easily produced.

INDUSTRIAL UTILIZATION

The double tube according to the present invention is preferable for medical use, particularly for the balloon catheter for PTCA or IABP.

We claim:

1. A double tube comprising:
    an outer tube having a lumen extending from a distal end of said outer tube to a proximal end of said outer tube;
    an inner tubes, which is provided within said outer tube, having a lumen extending from a distal end of said inner tube to a proximal end of said inner tube; and
    a connecting member which continuously extends from a distal end thereof to a proximal end thereof so that a part of an inner surface of said outer tube can connect to a part of an outer surface of said inner tube, wherein said connecting member is shaped to be able to separate said inner surface of said outer tube from said outer surface of said inner tube within a separable distance without damage, and wherein said connecting member is a longitudinal member having a height of between 0.05 to 3 mm and a thickness of between 0.03 to 0.8 mm.

2. The double tube as set forth in claim 1, wherein said longitudinal member has a notched portion which extends continuously along a longitudinal direction of said longitudinal member.

3. The double tube as set forth in claim 2, wherein said notched portion lies in a portion of said longitudinal member which is close to at least any one of said inner surface of said outer tube and said outer surface of said inner tube.

4. The double tube as set forth in claim 1, wherein a flexural rigidity of said outer tube is larger in said proximal end of said outer tube than in said distal end of said outer tube.

5. The double tube as set forth in claim 1, wherein a flexural rigidity of said inner tube is larger in said proximal end of said inner tube than in said distal end of said inner tube.

6. The double tube as set forth in claim 1, wherein a flexural rigidity of said outer tube and a flexural rigidity of said inner tube are both larger in said proximal end of said outer and inner tube, respectively, than in said distal end of said outer and inner tube, respectively.

7. The double tube as set forth in claim 1, wherein any one of said outer tube and said inner tube is comprised of a laminated layer tube which is layered with more than two kinds of material and wherein any one of a Young rate and a flexural rigidity of said laminated layer is formed to become smaller continuously from said proximal end of said outer and inner tube, respectively, to said distal end of said outer and inner tube, respectively.

8. The double tube as set forth in claim 1, wherein at least any one of said outer tube and said inner tube is a multi-layer tube formed by a layer comprised of a stiff material and a layer comprised of a soft material, and a cross-sectional area occupied by said layer comprised of said stiff material is smaller than a cross-sectional area occupied by said layer comprised of said soft material in said distal end of any one of said outer tube and said inner tube, respectively, and said cross-sectional area occupied by said layer comprised of said stiff material is larger than said cross-sectional area occupied by said layer comprised of said soft material in said proximal end of any one of said outer tube and said inner tube, respectively.

9. The double tube as set forth in claim 1, wherein said outer tube is comprised of a multi-layer tube comprised of an inside layer made of a stiff material and an outside layer made of a soft material, and a cross-sectional area occupied by said inside layer is smaller than a cross-sectional area occupied by said outside layer in said distal end of said outer tube, and said cross-sectional area occupied by said inside layer is larger than said cross-sectional area occupied by said outside layer in said proximal end of said outer tube.

10. The double tube as set forth in claim 1, wherein at least any one of said inner tube and said outer tube is comprised of a tube made of braided wire, a line density of said braided wire is made rough in said distal end of any one of said inner tube and said outer tube, respectively, and dense in said proximal end of any one of said inner tube and said outer tube, respectively.

11. The double tube as set forth in claim 1, wherein at least any one of said inner tube and said outer tube is comprised of a tube where soft material strip portions and stiff material strip portions extending in a strip form in an axial direction are alternately disposed in a circumferential direction, and a number of said soft material strip portions is made large in said distal end of any one of said inner tube and said outer tube, respectively, and small in said proximal end of any one of said inner tube and said outer tube, respectively.

12. The double tube as set forth in claim 1, wherein at least any one of said inner tube and said outer tube is comprised of a tube where soft material strip portions and stiff material strip portions extending in a strip form in an axial direction are alternately disposed in a circumferential direction, and a width of said circumferential direction of said soft material strip portions is made long in said distal end of any one of said inner tube and said outer tube, respectively, and short in said proximal end of any one of said inner tube and said outer tube, respectively.

13. A balloon catheter comprising:
    a double tube, wherein said double tube comprises:
        an outer tube having a lumen extending from a distal end of said outer tube to a proximal end of said outer tube;
        an inner tube, which is provided within said outer tube, having a lumen extending from a distal end of said inner tube to a proximal end of said inner tube; and
        a connecting member which continuously extends from a distal end thereof to a proximal end thereof so that one portion of an inner surface of said outer tube can connect to one portion of an outer surface of said inner tube, wherein a length of said outer tube is shorter than a length of said inner tube and said distal end of said inner tube is extended in a distal direction from said distal end of said outer tube, wherein said connecting member is shaped to be able to separate said inner surface of said outer tube from said outer surface of said inner tube within a separable distance without damage, and wherein said connecting member is comprised of a longitudinal member having a notched portion continuously along a longitudinal direction of said longitudinal member; and
    a balloon, wherein said balloon is formed by a cylindrical film and wherein a first end of said film is affixed to said distal end of said inner tube and a second end of said film is affixed to said distal end of said outer tube.

14. A process for producing a balloon catheter comprising the steps of
    cutting an outer tube of a double tube into a circular sliced portion at just the preferable distance from the distal end of the outer tube, the double tube being comprised of the outer tube having a lumen extending from the distal end to the proximal end, an inner tube which is provided within said outer tube and has a lumen extending from the distal end to the proximal end, and a connecting member continued from the distal end to the proximal end so that a part of an inner surface of said outer tube is connected to a part of an outer surface of said inner tube, separating a part of said outer tube from a part of said connecting member in a region from the distal end of the outer tube to said circular sliced portion, removing the part of said outer tube in the region from the distal end of said outer tube to said circular sliced portion, and affixing the one end of a cylindrical film as a balloon to said circular sliced portion of said outer tube and the other end of the film to the distal end of said inner tube.

* * * * *

UNITED STATES PATENT AND TRADEMARK OFFICE
CERTIFICATE OF CORRECTION

PATENT NO.: 5,833,672
DATED : Nov. 10, 1998
INVENTOR(S): KAWATA et al.

It is certified that error appears in the above-identified patent and that said Letters Patent is hereby corrected as shown below:

On the title page: Item

[22] PCT Filed: please change the date from Nov. 11, 1995 to

--Dec. 11, 1995--

Signed and Sealed this

Thirtieth Day of March, 1999

Attest:

Q. TODD DICKINSON

*Attesting Officer*  *Acting Commissioner of Patents and Trademarks*